United States Patent [19]

Kirschner et al.

[11] Patent Number: 5,665,307
[45] Date of Patent: Sep. 9, 1997

[54] AQUEOUS DISINFECTING AGENT

[75] Inventors: Ulrich Kirschner, Morfelden-Walldorf; Thomas Pohl, Bad Homburg v. d. H., both of Germany

[73] Assignee: Fresenius AG, Bad Homburg v. d. H., Germany

[21] Appl. No.: 483,822

[22] Filed: Jun. 7, 1995

Related U.S. Application Data

[63] Continuation-in-part of Ser. No. 262,944, Jun. 21, 1994, abandoned, which is a continuation of Ser. No. 857,847, Mar. 26, 1992, abandoned.

[30] Foreign Application Priority Data

Mar. 27, 1991 [DE] Germany .......................... 41 10 078.6
Jan. 6, 1992 [DE] Germany .......................... 42 00 066.1

[51] Int. Cl.$^6$ .......................... A01N 25/02; A01N 37/02; C07C 59/265
[52] U.S. Cl. .............................. 422/28; 562/584
[58] Field of Search .................. 422/1, 28, 292; 562/584

[56] References Cited

FOREIGN PATENT DOCUMENTS 0148709  7/1985  European Pat. Off. .
2103089  2/1983  United Kingdom .

OTHER PUBLICATIONS

Block, Seymour S. *Disinfection, Sterilization, and Preservation*, 3rd ed, pp. 474–475 1983.
Wisniewski, Jerzy. "Comparison of Virucidal Action of Disinfectants of aphthous fever virus," pp. 1–9 of translated article 1971.

*Primary Examiner*—Robert J. Warden
*Assistant Examiner*—E. Leigh Dawson
*Attorney, Agent, or Firm*—Omri M. Behr, Esq.

[57] ABSTRACT

There is provided a disinfecting material effective against Hepatitis B, including citric acid and optionally malic acid and/or lactic acid. This virucidal material is not only environmentally acceptable and has low human toxicity, but has high effectiveness at relatively low temperatures for comparatively short times. This disinfecting material containing aqueous citric acid is particularly effective in critical clinical areas.

6 Claims, No Drawings

AQUEOUS DISINFECTING AGENT

RELATED APPLICATIONS

This application is a continuation-in-part of application Ser. No. 08/262,944 filed Jun. 21, 1994, which is a continuation of application Ser. No. 07/857,847 filed Mar. 26, 1992—now abandoned.

FIELD OF THE INVENTION

An aqueous disinfecting agent which is effective against bacterial spores and hepato-viruses, in particular hepatitis B viruses.

DISCUSSION OF THE PRIOR ART

It is known that in order to achieve, by purely thermal means, the deactivation of hepatitis B viruses, there is required a temperature of 100° C. for a time of 10 minutes, or alternatively, a heating time of 10 hours at temperature of 60° C. and for the inactivation of hepatitis A viruses, a single minute at 98° C. is adequate (see K. H. Wallhauser [in German] "Practice of Sterilization, Disinfection, Conservation", 4th Edition, 1988, Georg Theime, Publishers, Stuttgart-New York, pp. 75, et seq., [Table 31]). It is further known that bacteria are already deactivated at 60° C. Because of the comparatively high temperatures needed, as well as the long process time, this particular mode of disinfection is unsuitable for heat labile apparatuses made of synthetic materials, for example dialysis apparatuses, and is therefore impractical. Therefore at the present time, the disinfection of apparatuses and instruments by submerging same for at least 6 hours in a 3% formalin solution is utilized. But unfortunately in order to avoid a totally undesired adsorption of this material on the polymeric surfaces, very careful rinsing is required (see K. H. Wallhauser, supra., page 76). Quite apart from the environmental unsoundness and toxicity of formalin, such process times are not highly acceptable in practice.

It had previously been shown that bovine parvo virus (BPV, Sp. Haden), is very resistant to chemical disinfection. Even at a temperature of 30° C. and utilizing a 3% concentration, for 6 hours of acetic, propionic, citric or even formic acids, which are effective at higher temperatures, is ineffective. (See Hyg. and Med. 15 (1990) page 313–317). Furthermore, the inactivation of hepatitis A and hepatitis B virus at acid pH's has not been noted. (See. K. H. Wallhauser, supra., pages 79-80).

Block (Disinfection, Sterilization and Preservation, 3rd. ed 1983 at p. 474) contains vague statements there is no evidence that Hepatitis viruses are unusually resistant to chemical agents. This opinion is not supported by current thinking. Glutaraldehyde disinfectants (ULTRASCOPE/ CIDEX) which is a high level disinfectant and known to control "naked" viruses, which are generally considered the most resistant is only minimally effective against Hepatitis B, now considered to be an encapsulated viruses. Since encapsulated viruses are generally considered to be at the intermediate sensitivity level, Hepatitis B clearly is in an unpredictable category. It should further be noted that at p. 666 Block notes that citric acid is a less effective antimicrobial than other acids and at p. 739 designates glutaraldehyde as a highly effective sporicide.

Hossain, et al. British patent 2 103 089 teaches the use of carboxylic acids specifically as virucides. However, Hossain, et al. discusses a method for interrupting or preventing the spread of respiratory viruses. Examples of common respiratory viruses according to Hossain embrace for example, rhino viruses, parainfluenza viruses and adeno viruses. Among these respiratory viruses are rhino viruses which are so called naked viruses. From the point of view of disinfection, such naked viruses are much more difficult to inactivate than encapsulated viruses. Nevertheless, it cannot be generally said that a disinfectant material which controls a particular member of a viral group is necessarily effective against other members of the same viral group at the same level of aggressiveness.

With respect to bacterial spores, it is known that they are highly temperature resistant, i.e. up to 120° C. and are also substantially chemoresistant. That it requires acids of the strength of peracidic acid to inactive them.

It is further known that glutaraldehyde based disinfectant materials which Block considers as the most effective disinfecting materials against, i.e. high level disinfectants are only effective against bacterial spores after a long contact time and in the absence of additional organic materials. It has further been found that glutaraldehyde based disinfectants are effective against naked polio viruses at a 2% concentration for 30 minutes whereas, the same conditions absolutely ineffective against hepato B viruses. Only the higher concentration of 3% for 2 hours, or 5% for 30 minutes are these materials effective against hepato B viruses.

Wisniewski's use of citric against foot and mouth disease has no teaching with respect to Hepatitis B (Med. Weter. 27(8), 480–482, (1971)). Foot and mouth disease is caused by an aphtho fever virus. Aptho virus belongs to the genus of Picornaviridi, which includes, inter alia, the rhino virus of Hossain, but does not includes Hepatitis B viruses. Hence, Wisniewski cannot be considered a teaching of the use of citric acid and similar acids against Hepatitis B virus.

SUMMARY OF THE INVENTION

This material is useful for disinfecting thermolabile medicinal instruments and apparatuses, as well as parts thereof. The invention is further concerned with a process for disinfecting surfaces contaminated with bacterial spores and hepato viruses, in particular hepato virus B, where such surfaces are found on thermolabile medicinal instruments and apparatuses and parts thereof. Surfaces are internal and external surfaces, including inner surfaces of tubing (for example, the water-circuit of a dialysis machine).

The purpose of the invention is to find an environmentally sound disinfecting material effective against hepato viruses, in particular hepatovirus B and bacterial spores, which are highly effective in a desirably short process time and which require comparatively low process temperatures so that they may be utilized for the disinfection of thermolabile medicinal instruments and apparatuses and parts thereof, for example, they would be highly suitable for the disinfection of dialysis apparatuses.

A further purpose of the present invention is to open up new clinical areas for disinfection with aqueous disinfecting materials, whereby this new area is provided with high efficacy accompanied by low operating times and desirably low operating temperatures. In particular, clinical areas should be considered in which the use of aqueous disinfecting materials has not previously been indicated, wherein the risk of infection was seen to be large and high effectiveness is necessary.

It is well known that in the field of dialysis, the danger of hepatitis infection is a substantial problem.

It has now been found that the activity of hepatitis B viruses can be reduced to a level which is no longer detectable in the DNA polymerase test by exposure to a 1.5% by weight aqueous solution of citric acid at 20° C. or a 0.4% solution at 60° C. for an exposure time of nearly 5 minutes.

The purpose of the invention is to provide a disinfecting material, effective against bacterial spores and hepatoviruses, in particular hepatitis B viruses, which is aqueous and can be utilized as a disinfection material for dialysis apparatuses, in particular thermolabile medicinal instruments and apparatuses and parts thereof, which can be characterized by containing citric acid as a viricidal agent.

This new disinfecting material can be distinguished from the previously utilized formaldehyde as being environmentally acceptable as a viricidal material. Above all, it makes possible a far shorter processing time at a simultaneously lower temperature.

DESCRIPTION OF THE PREFERRED EMBODIMENTS

The invention comprises a process of disinfecting surfaces particularly those of thermolabile medicinal instruments and apparatuses and parts thereof, which have been infected by bacterial spores and/or hepatoviruses, in particular hepatitis B virus. In this process for the inactivation of hepatoviruses these surfaces are treated at a temperature of between about 20° C. to about 75° C, for a time of between about 1 to between about 5 minutes, with an aqueous solution which comprises citric acid in viricidally effective concentrations. In a particularly preferred embodiment of the disinfecting material in accordance with the present invention, there is utilized citric acid as the viricidally effective material, suitably in a concentration of between 0.05 to 3 wt. %, preferably between 0.2 to 2.5 wt. %, especially between 0.4 and 0.6 wt. %.

Since the disinfecting action increases with an increase in temperature and operating time, utilizing the aforementioned upper limits of citric acid concentration enables the utilization of short process times, for example 5 to 10 minutes, and low temperatures, for example ambient temperature, while utilizing the lower limits requires higher temperatures, suitably 60° C. and longer exposure times (15 minutes and more).

The efficacy of citric acid can be improved by the addition thereto of other acids in particular, malic acid, lactic acid and/or tartaric acid. Additionally, this reduces the possibility of resistance development by the bacterial spores or viruses. Furthermore, this assists the reduction of any tendency towards crystallization. These acids may be utilized in quantities of between 5 and 20 wt. %, preferably about 10 wt. % of the citric acid content.

The disinfecting material of the present invention is desirably provided in the form of an acid concentrate in which an embodiment comprising 50% by weight of citric acid is preferred. This concentrate is then reduced to the desired concentration at the time and place of utilization with sterile deionized water to a lower concentration, suitably to about 2 wt. %.

A further desirable embodiment of the concentrate comprises about 21 wt. % of citric acid, 2 wt. % of lactic acid and 2 wt. % of malic acid. As has been shown (see examples below), even at 1.5 wt. % of aqueous citric acid solution, the total inactivation of hepatitis B viruses occurs during a process time of merely 5 minutes at an operating temperature of only 20° C. In a particularly desirable embodiment of the inventive process, contaminated surfaces may be treated with at least a 1.5 wt. % solution, suitably a 1.5 wt. % citric acid solution at an operating temperature of between 20 and 75° C, suitably at 20° C. during a process time of at least 5 minutes and particularly 5 minutes. A further embodiment of the invention comprises the use of aqueous citric acid containing disinfecting materials for the inactivation of bacterial spores. Suitably at 70° C.

The following examples serve to further explain the invention.

Except where otherwise indicated the percentage indications refer to percentages by weight.

EXAMPLE 1

Test Method

The hepatovirocidal properties of a 2% citric acid solution are conducted upon a suspension at 20° C. and 75° C.

B—Background

Since in vitro culture systems for hepatitis B virus (HBV) are not yet available, the determination of HBV infectivity in the present experiments was carried out with the DNA polymerase test. The DNA polymerase provides a good marker for the structural integrity of the virus and can therefore serve as an indirect marker for the infectivity thereof.

C—Preparation of Dane* Particle Suspension

In order to concentrate and partially clean the utilized Dane particles, 240 ml. of serum from a subject with chronic HBsAg (Hepatitis B surface antigen) carrier status and proof of HBcAg (Hepatitis B core antigen) and the DNA polymerase were centrifuged together in a type SW28 Rotor at 25,00 rpm for 16 hours at 4° C. The sediment was taken up in 2 ml. of 0.1M phosphate buffered saline with 0.01% (w/v) serum albumin and layered with 4 ml. of a 20% solution (w/w) of saccharose. A centrifugation in a type 60 TI Rotor at 50,000 rpm for 2 hours was then instituted. After decantation, the Dane particles were taken up in 0.1M Tris buffer (Ph 7.4). As a measure of the concentration of the Dane particles, there followed a determination of the DNA polymerase activity in accordance with the method of Kaplan, et al. (J. Virol. 12 (1973) page 995 et seq. After addition of all four desoxy ribonucleoside triphosphates, the newly synthesized DNA was measured in that the radioactivity was determined in a liquid scintillation counter.

*A Dane particle is the designation for the virion of the Hepatitis B virus, probably the virus itself. The more compact core is the nucleo capside and contains the $HB_cAg$ and is immunofluoroscopically detectable in the liver matrix.

D—Disinfection Experiments

In the following experiments, there was utilized as disinfecting material, a 2% aqueous solution of citric acid in which commercially available citric acid (obtained from Merck, catalog no. 244) was taken up in doubly distilled water. The Ph value of the 2% solution was 2.2.

The disinfectant material was placed in polyallomer tubes and the test carried out at 20° C. and 70° C. in accordance with the guidelines of the German Federal Health Office and the German Association for Combatting Viral Diseases (DVV). The experiment comprises 1 part by volume of Dane particle suspension, 1 part by volume of 0.01M Tris buffer and 8 parts by volume of the 2% citric acid solution as disinfecting material. In the experiments with albumin, loading of the Tris buffer was replaced by a 2% solution bovine serum albumin (from Behring Werke) or by fetal calf serum (FKS from Boehringer Mannheim).

There further followed an experiment without the addition of viruses in order, by this means, to determine a non-specificity in the DNA polymerized test by the disinfecting material utilized.

As positive control, there was utilized a 1.75 wt. % formaldehyde solution (Ph 7.0). This solution had previously indicated anti-HBV efficacy in DNA polymerase test.

Immediately after the completion of the process time, dilution with 2.4 ml. of 0.1M Tris buffer was carried out in order to stop the disinfecting action by dilution. Thereafter, there were added by layering, 2 ml. of 20% by weight. of saccharose solution. Centrifugation followed in a centrifuge of type SW60 with a Ti Rotor at 50,000 rpm at 4° C. for 2 hours.

After decantation of the supernate and drying in a desiccator, the pellet was resuspended in 50 microliters of 0.01M Tris buffer and 25 microliters thereof, utilized for determination by of DNA polymerase activity in this test. In accordance with a further experiment, there was utilized a 0.4 wt. % citric acid solution at 60° C. and a mixture of 0.6 wt. % citric acid, 0.06 wt. % of lactic acid and 0.06 wt. % of malic acid to determine the disinfectivity at 60° C.

E—Results

Tables 1 and 2 show the results of experiments carried out on partially cleaned Dane particles with a 2% by weight aqueous citric acid solution as the disinfecting material. The results obtained with a 1.5 wt. % aqueous formaldehyde solution as control are shown in Table 3. The Dane particle suspension utilized was so provided that a 100 microliter solution of this solution gave about 20,000 counts per minute. This insured that the HBV concentration in the test portion was about $10^8$ Dane particles.

Table 1 shows the results obtained by the application of the 2% by weight citric acid solution in accordance with this invention, as the disinfecting material. The measurements were carried out after an application time of 5, 15 and 30 minutes in order to obtain the result reflecting the kinetics of the operation. As initial data for the reduction of HBV activity, values were utilized which were obtained in the presence of Tris buffer. The background values were also measured with respect to the influence of citric acid on the test system, without the presence of viruses. Thus, one was able to obtain the base-line value. Utilizing the 2% by weight citric acid solution, the values of 10, 10 and 12 counts per minute were found in the three selected examples.

Table 1 shows that already after 5 minutes of processing, it was possible to find counts in the samples which were carried out with Tris buffer and without the presence of viruses. This provided the base-line value below which no viral activity was detectable in the DNA polymerase test. This result is also valid for the samples where albumin was present in the test sample.

In order to determine the effect of the disinfecting material and to study the impact of temperature separately, further experiments were carried out. Thus, the effectiveness of the 2% citric acid solution at 20° C. as well as the influence of temperature without the addition of disinfecting material is also studied. The corresponding results are set forth in Table 2.

From this Table, it may be determined that a 1.5 wt. % citric acid solution is already able, at 20° C., to significantly reduce the viral titer. Even here after 5 minutes, it was possible to obtain count values which lay at the level of the controls and thus to establish the background levels. Furthermore, it was possible to determine that the influence of temperature alone at 75° is not sufficient to totally eliminate viral activity in the DNA polymerase test. Even after 5 and 15 minutes of process time, the values were found which were significantly higher than the values in the citric acid addition experiments. It is of interest to note that the highest counts were obtained in the presence of fetal calf serum.

In the inactivating experiments, 1.5 wt. % formaldehyde solution was utilized as a control. After earlier experiments had shown that a 0.5 wt. % solution thereof was not able, after 60 minutes process time, to significantly reduce values of viral titer to meet the guidelines of the German Federal Health Office and the German Association for Combatting Viral Diseases for determining the viricidal activity of chemical disinfecting materials.

The experimental results obtained in the formaldehyde experiments are shown in Table 3. From this, it may be noted that a 60 minute process time is necessary to reduce the HBV activity to such a level that no positive readings are obtained in the DNA polymerase test. That is to say, after this time, a count of 24 was obtained which is also the value obtained in the so-called "blank" control experiments without addition of viral material.

In Table 4, results are shown for experiments at 60° C. with a 0.4 wt. % solution of citric acid as well as with a mixture of 0.6 wt. % citric acid, mixed with 0.06% by weight of malic acid and 0.05 wt. % of lactic acid.

Explanation of the samples utilized in tables 1 and 2 Dane particle controls

I. Dane particle+2×distilled water+Tris buffer

II. Dane particle+2% albumin+Tris buffer

III. Dane particle+FCS+Tris buffer

Disinfection material control

I. Tris buffer+2×distilled water+disinfection material.

II. Tris buffer+2% albumin+disinfection material

III. Tris buffer+FCS+disinfection material.

Inactivation Sample

I. Dane particle+2×distilled+disinfection material.

II. Dane particle+2% albumin+disinfection material

III. Dane particles+FCS+disinfection material.

Relative Volume of All Samples I through III

One part by volume+1 part by volume+9 parts by volume. Disinfection material=2% aqueous citric acid solution, FCS=fetal calf serum.

TABLE 1

HBV Inactivating Properties of a 2% Citric Acid Solution at 75° C. Results are expressed as Counts per Minute (cpm).

| Process Time in Minutes | Dane Particles — Controls in | | | Disinfection Material — Controls | | | Inactivation Material (2% Citric Acid) | | |
|---|---|---|---|---|---|---|---|---|---|
| | I | II | III | I | II | III | I | II | III |
| 5 | 4788 | 4666 | 4781 | n/a | n/a | n/a | 11 | 8 | 9 |
| 15 | n/a | n/a | n/a | n/a | n/a | n/a | 12 | 9 | 7 |
| 10 | 4818 | 4517 | 4619 | 10 | 12 | | 13 | 10 | |

*n/a — not carried out.

TABLE 2

HBV — inactivation properties of a citric acid solution at 20° C. as well as thermostability of HBV at 75° C. Results in Counts per Minute (cpm).

| Process Time in Minutes | Citric Acid (2%) | | | Tris Buffer at 75° C. | | |
|---|---|---|---|---|---|---|
| | I | II | III | I | II | III |
| 5 | 14 | 18 | 11 | 135 | 240 | 275 |
| 15 | 9 | n/a | n/a | 105 | 190 | 220 |
| 30 | 10 | n/a | n/a | n/a | n/a | n/a |

*n/a — not carried out.

TABLE 3

HBV — Inactivation properties of Formaldehyde (Control). Results in Counts Per minute (cpm)

| Process Time in Minutes | Formaldehyde (1.75%) |
|---|---|
| 1 | n/a |
| 15 | 485 |
| 30 | 121 |
| 60 | 24 |

*n/a — not carried out.

TABLE 4

HAV Inactivating Properties of an aqueous:
a) 0.4% citric acid solution.
b) 0.6% citric acid, 0.02% malic acid, 0.06% lactic acid.
Tests at 60° C.

| Process Time in | Dane Particles — Control | | | Inactivation Material (a) | | | Inactivation Material (b) | | |
|---|---|---|---|---|---|---|---|---|---|
| Minutes | I | II | III | I | II | III | I | II | III |
| 1 | n/a | n/a | n/a | 410 | 302 | 358 | 354 | 280 | 421 |
| 6 | n/a | n/a | n/a | 107 | 99 | 110 | 15 | 19 | 18 |
| 10 | 4543 | 4782 | 4490 | 12 | 13 | 8 | 10 | 15 | 6 |

*n/a — not carried out.

EXAMPLE 2

Bacteriocidal effects of a disinfecting material comprising citric acid

A—Test Method

The bacteriocidal effects of a disinfecting material comprising 0.25, 0.5, 1.0 and 1.5 wt. %, wherein 80 wt. % of the active material is citric acid and 10% each by weight of the active material are lactic acid and malic acid are quantitatively determined in a suspension test at 50° C., at 60° C., and at 70° C. in accordance with the protocols of the German Society for Hygiene and Microbiology (DGHM).

The bacteriocidal properties of Legionella pneumophilia SG1 were also determined. The combination utilized for the activation comprised 3% by weight Tween 80, 3% saponin, 0.1% histidine and 0.1% cystine. As culture medium there was utilized BCYE alpha agar and culturing took place for 14 days at 25° C. in a $CO_2$ atmosphere.

The results are set forth in Table 5. This shows that at the selected temperature of greater than 50° C., the disinfecting solution is effective against legionella at the chosen concentration. Even low concentrations are sufficient at a temperature of 70° C. to meet the requirements of the German Society for Hygiene and Microbiology.

TABLE 5

| Time (in Mins) | 5 | 10 | 15 |
|---|---|---|---|
| Without Albumin loading (1/2.3.1) Test Organism — Leg. pneumophila SG 1 | | | |
| Control (log.) In WSH (50° C.) | 7.33 | 7.20 | 7.11 |
| Control (log.) in WSH (60° C.) | 4.47 | 3.42 | 2.15 |
| Control (log.) in WSH (70° C.) | 2.15 | 1.30 | 0.0 |
| Control (log.) in WSH (22° C.) | 7.48 | 7.43 | 7.33 |

| | Reduction Factors (log.) after: | | |
|---|---|---|---|
| Time (in mins) | 5 | 10 | 15 |
| Concentration (%) at | | | |
| Reaction Temp. (50° C.) | | | |
| 1.5 | 5.70 | 6.13 | ≧6.33 |
| 1.0 | 2.57 | 5.17 | 6.03 |
| 0.5 | 2.22 | 3.0 | 4.95 |
| 0.25 | 1.42 | 2.05 | 2.23 |
| Reaction Temp. (60° C.) | | | |
| 1.5 | ≧6.48 | ≧6.43 | ≧6.33 |
| 1.0 | ≧6.48 | ≧6.43 | ≧6.33 |
| 0.5 | ≧6.48 | ≧6.63 | ≧6.33 |
| 0.25 | 4.94 | 5.22 | 6.03 |
| Reaction Temp. (70° C.) | | | |
| 1.5 | ≧6.48 | ≧6.43 | ≧6.33 |
| 1.0 | ≧6.48 | ≧6.43 | ≧6.33 |
| 0.5 | ≧6.48 | ≧6.43 | ≧6.33 |
| 0.25 | 5.57 | 5.65 | 5.73 |

EXAMPLE 3

Sporicidal properties of a disinfecting solution comprising citric acid

A—Test Method

The test method of Example 2 was utilized to determine the sporicidal properties of the disinfecting solution having a content of active material of 0.5, 1.0, and 1.5 wt. %. Also here the active combination comprised 80% citric acid, 10% malic acid and 10% lactic acid. The sporicidal properties were determined at three temperatures: 73° C.; 83° C. and 90° C., with respect to Bacillus subtilis ATCC 6051, in a water bath in accordance with the quantitative suspension test set forth by the German Society of Hygiene and Microbiology. Particular attention was paid to the guidelines of the DGHM. The spore count of the starting material per ml. was 9.80 log units. The inactivation mixture also comprised 3% Tween 80, 3% saponin, 0.1% histidine and 0.1% cystine.

The results of the test with sporicidal effectiveness of the disinfecting material are set forth in Table 6. It will be noted that the disinfecting material is also very effective against bacterial spores at 93° C.

TABLE 6

| Time (in Mins) | 5 | 10 | 15 |
|---|---|---|---|
| Control (log.) In WSH (73° C.) | 6.69 | 6.67 | 6.47 |
| Control (log.) in WSH (83° C.) | 6.40 | 6.40 | 6.27 |
| Control (log.) in WSH (93° C.) | 6.51 | 6.11 | 5.90 |
| Control (log.) in WSH (R.T) | 6.71 | 6.62 | 6.59 |

| | Reduction Factor (log.) after: | | |
|---|---|---|---|
| Time (min.) | 5 | 10 | 15 |
| Concentration (%) at | | | |
| Reaction Temp. (73° C.) | | | |
| 1.5 | 1.50 | 1.88 | 1.99 |
| 1.0 | 0.88 | 1.85 | 1.93 |
| 0.5 | 0.72 | 0.73 | 1.16 |
| Reaction Temp. (83° C.) | | | |
| 1.5 | 2.39 | 3.82 | 3.85 |
| 1.0 | 2.20 | 3.34 | 3.35 |
| 0.5 | 1.80 | 2.74 | 2.86 |
| Reaction Temp. (93° C.) | | | |
| 1.5 | 3.90 | 4.20 | 5.29 |
| 1.0 | 3.84 | 3.90 | 4.33 |
| 0.5 | 3.36 | 3.36 | 4.17 |

EXAMPLE 4

Determination of effectiveness of ULTRASCOPE against Hepatitis B

Test Method

The hepatovirocidal properties of a 1.5, 3 and 5% glutaraldehyde (ULTRASCOPE/CIDEX) solution are conducted upon a suspension at 20° C.

9

A—Preparation of Dane* Particle Suspension

In order to concentrate and partially clean the utilized Dane particles, 240 ml. of serum from a subject with chronic Hbsag (Hepatitis B surface antigen) carrier status and proof of Hbcag (Hepatitis B core antigen) and the DNA polymerase were centrifuged together in a type SW28 Rotor at 25,00 rpm for 16 hours at 4° C. The sediment was taken up in 2 ml. of 0.01M phosphate buffered saline with 0.1% (w/v) serum albumin and layered with 4 ml. of a 20% solution (w/w) of saccharose. A centrifugation in a type 60 TI Rotor at 50,000 rpm for 2 hours was then instituted. After decantation, the Dane particles were taken up in 0.01M Tris buffer (Ph 7.4). As a measure of the concentration of the Dane particles, there followed a determination of the DNA polymerase activity in accordance with the method of Kaplan, et al. (J. Virol. 12 (1973) page 995 et seq. After addition of all four desoxy ribonucleoside triphosphates, the newly synthesized DNA was measured in that the radioactivity was determined in a liquid scintillation counter.

*A Dane particle is the designation for the virion of the Hepatitis B virus, probably the virus itself. The more compact core is the nucleo capside and contains the $HB_cAg$ and is immunofluoroscopically detectable in the liver matrix.

D—Disinfection Experiments

In the following experiments, there was utilized as disinfecting material, 1.5, 3.0 and 5.0% aqueous solution of glutaraldehyde, commercially available as ULTRASCOPE/ CIDEX, taken up in doubly distilled water.

The disinfectant material was placed in polyallomer tubes and the test carried out at 20° C. in accordance with the guidelines of the German Federal Health Office and the German Association for Combatting Viral Diseases (DVV). The experiment comprises 1 part by volume of Dane particle suspension, 1 part by volume of 0.01M Tris buffer and 8 parts by volume of the 2% ULTRASCOPE solution at 1.25 times the desired concentration as disinfecting material. In the experiments with albumin, loading of the Tris buffer was replaced by a 2% solution bovine serum albumin (BSA, from Behring Werke) or by fetal calf serum (FKS from Boehringer Mannheim).

There further followed an experiment without the addition of viruses in order, by this means, to determine a nonspecificity in the DNA polymerized test by the disinfecting material utilized.

As positive control, there was utilized a 1.75 wt. % formaldehyde solution (Ph 7.0). This solution had previously indicated anti-HBV efficacy in DNA polymerase test.

Immediately after the completion of the process time, dilution with 2.4 ml. of 0.01M Tris buffer was carried out in order to stop the disinfecting action by dilution. Thereafter, there were added by layering, 2 ml. of 20% by weight of saccharose solution. Centrifugation followed in a centrifuge of type SW60 with a Ti Rotor at 50,000 rpm at 4° C. for 2 hours.

After decantation of the supernate and drying in a desiccator, the pellet was resuspended in 50 microliters of 0.01M Tris buffer and 25 microliters thereof, utilized for determination by of DNA polymerase activity in this test.

E—Results

In the inactivating experiments of Table 1, 1.5 wt. % formaldehyde solution was utilized as a control. After earlier experiments had shown that a 0.5 wt. % solution thereof was not able, after 60 minutes process time, to significantly reduce values of viral titer to meet the guidelines of the German Federal Health Office and the German Association for Combatting Viral Diseases for determining the viricidal activity of chemical disinfecting materials.

The experimental results obtained in the formaldehyde experiments are shown in Table 7. From this, it may be noted that a 60 minute process time is necessary to reduce the HBV activity to such a level that no positive readings are obtained in the DNA polymerase test. That is to say, after this time, a count of 19 was obtained which is also the value obtained in the so-called "blank" control experiments without addition of viral material.

Tables 8–10 show the results of experiments carried out on partially cleaned Dane particles with a 1.5, 3.0, and 5.0% by weight ULTRASCOPE solution as the disinfecting material during test periods of from 15 to 120 minutes. Dane particle suspension utilized was so provided that a 100 microliter solution of this solution gave about 20,000 counts per minute. This insured that the HBV concentration in the test portion was about $10^8$ Dane particles.

In order to determine the effect of the disinfecting material on the test system itself, further experiments were carried out. Thus, the influence of the ULTRASCOPE without the viral materials was found to be of the order of 3–9 cpm.

Table 8 shows the results obtained by the application of the 1.5% by weight ULTRASCOPE solution, as the disinfecting material. The measurements were carried out after an application time of 15, 30, 60 and 120 minutes in order to obtain the result reflecting the kinetics of the operation. Utilizing the 1.5% by weight ULTRASCOPE solution, even after 2 hours viral activity was not eliminated. Even without addition of albumin a 89 counts per minute was found corresponding to a residual activity of 1.78%.

Explanation of the samples utilized in tables 8,9 and 10

Dane particle controls

I. Dane particle+2×distilled water+Tris buffer

II. Dane particle+2% albumin+Tris buffer

III. Dane particle+FCS+Tris buffer

Disinfection material control

I. Tris buffer+2×distilled water+disinfection material.

II. Tris buffer+2% albumin+disinfection material

III. Tris buffer+FCS+disinfection material.

Inactivation Sample

I. Dane particle+2×distilled+disinfection material.

II. Dane particle+2% albumin+disinfection material

III. Dane particles+FCS+disinfection material.

Relative Volume of All Samples I through III 1 part by volume+1 part by volume+8 parts by volume.

Disinfection material=1.5, 3.0, 5.0% aqueous ULTRASCOPE solution, FCS=fetal calf serum.

TABLE 7

HBV — Inactivation properties of Formaldehyde (Control).
Results in Counts Per minute (cpm)

| Process Time in Minutes | Formaldehyde (1.75%) |
|---|---|
| 5 | 1148 |
| 15 | 671 |
| 30 | 213 |
| 60 | 19 |

*n/a — not carried out.

TABLE 8

HBV Inactivating Properties of a 1.5% ULTRASCOPE Solution at 20° C. Results are expressed as Counts per Minute (cpm).

| Process Time in Minutes | Dane Particles — Controls | | | Disinfection Material — Controls | | | Inactivation Material (1.5% ULTRASCOPE) | | |
|---|---|---|---|---|---|---|---|---|---|
| | I | II | III | I | II | III | I | II | III |
| 5 | 5046 | 4977 | 4917 | n/a | n/a | n/a | n/a | n/a | n/a |
| 15 | n/a | n/a | n/a | n/a | n/a | n/a | 1284 | n/a | n/a |

TABLE 8-continued

HBV Inactivating Properties of a 1.5% ULTRASCOPE Solution at 20° C. Results are expressed as Counts per Minute (cpm).

| Process Time in Minutes | Dane Particles — Controls | | | Disinfection Material — Controls | | | Inactivation Material (1.5% ULTRASCOPE) | | |
|---|---|---|---|---|---|---|---|---|---|
| | I | II | III | I | II | III | I | II | III |
| 30 | n/a | n/a | n/a | — | — | — | 678 | 1019 | 1127 |
| 60 | 4971 | 5011 | 4819 | 7 | 4 | 5 | 209 | 318 | 420 |
| 120 | n/a | n/a | n/a | — | — | — | 89 | n/a | n/a |

*n/a — not carried out.

TABLE 9

HBV Inactivating Properties of a 3.0% ULTRASCOPE Solution at 20° C. Results are expressed as Counts per Minute (cpm).

| Process Time in Minutes | Dane Particles — Controls | | | Disinfection Material — Controls | | | Inactivation Material (3.0% ULTRASCOPE) | | |
|---|---|---|---|---|---|---|---|---|---|
| | I | II | III | I | II | III | I | II | III |
| 5 | 4791 | 5108 | 4999 | n/a | n/a | n/a | n/a | n/a | n/a |
| 15 | n/a | n/a | n/a | n/a | n/a | n/a | n/a | n/a | n/a |
| 30 | n/a | n/a | n/a | — | — | — | 381 | n/a | n/a |
| 60 | n/a | n/a | n/a | 9 | 6 | 7 | 89 | 181 | 212 |
| 120 | 4854 | 4877 | 4943 | — | — | — | 6 | 18 | 34 |

*n/a — not carried out.

TABLE 10

HBV Inactivating Properties of a 5.0% ULTRASCOPE Solution at 20° C. Results are expressed as Counts per Minute (cpm).

| Process Time in Minutes | Dane Particles — Controls | | | Disinfection Material — Controls | | | Inactivation Material (5.0% ULTRASCOPE) | | |
|---|---|---|---|---|---|---|---|---|---|
| | I | II | III | I | II | III | I | II | III |
| 5 | 4788 | 4979 | 5011 | n/a | n/a | n/a | n/a | n/a | n/a |
| 15 | n/a | n/a | n/a | n/a | n/a | n/a | 341 | n/a | n/a |
| 30 | n/a | n/a | n/a | — | — | — | 101 | 120 | 164 |
| 60 | 4857 | 4888 | 4963 | 4 | 3 | 8 | 7 | 6 | 8 |
| 120 | n/a | n/a | n/a | — | — | — | 5 | 7 | 9 |

*n/a — not carried out.

In experiments with 3% solution it was shown that even after one hour of exposure there was still residual viral activity (Table 8) after two hours without the addition of albumin it was possible to measure a value in which the corresponding disinfection controls lay. Nevertheless, it was possible to show residual levels of activity in both portions with albumin and fetal calf serum.

Table 10 shows considerably stronger virucidal activity with 5% Ultrascope. Here it was shown that after 60 minutes exposure the count numbers dropped so decidedly that no proof of enzymic activity could be found. This applies to all three test samples.

In sum, it was found that ultrascope acts as a disinfectant material for Hepatitis B as a 3% solution at 2 hours, or in the presence of albumin as a 5% solution within one hour.

We claim:

1. A process for the disinfection of a hepatovirally contaminated surface which comprises contacting a hepatitis B contaminated surface with an aqueous solution, consisting essentially of, as sole virucidal components, a member of the group consisting of citric acid and one or more components selected from the group consisting of lactic acid, malic acid and tartaric acid wherein the concentration of any of the additional acid components is between 5 and 20 wt. % of the citric acid, at a temperature of between about 20° C. to about 75° C. for at least 5 minutes.

2. The process according to claim 1, wherein the surface is the surface of a temperature sensitive medicinal apparatus.

3. The process according to claim 1 wherein the concentration of citric acid is between about 0.05 to about 3 wt. %.

4. The process according to claim 3 wherein the concentration of citric acid is from about 0.2 to about 2.5 wt. %.

5. The process according to claim 4 wherein the concentration of citric acid is from about 0.4 to about 0.6 wt. %.

6. The process according to claim 1 wherein the acidic components of the aqueous solution material are provided as an aqueous concentrate of 21% citric acid, 2% malic acid and 2% lactic acid, all by weight, diluted 1:10 with water.

* * * * *